(12) United States Patent
Urbahn et al.

(10) Patent No.: US 8,731,640 B2
(45) Date of Patent: *May 20, 2014

(54) FLUID PATH SYSTEM FOR DISSOLUTION AND TRANSPORT OF A HYPERPOLARIZED MATERIAL

(75) Inventors: John Arthur Urbahn, Saratoga Springs, NY (US); Jan Henrik Ardenkjaer-Larsen, Frederiksberg C (DK); Andrew Michael Leach, Clifton Park, NY (US); Eric John Telfeyan, Delanson, NY (US); David Key Dietrich, Niskayuna, NY (US); David Brandon Whitt, Long Beach, CA (US); Peter Miller, Ledyard, CT (US); Ernst Wolfgang Stautner, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/350,189

(22) Filed: Jan. 13, 2012

(65) Prior Publication Data
US 2012/0117985 A1 May 17, 2012

Related U.S. Application Data

(63) Continuation-in-part of application No. 11/692,642, filed on Mar. 28, 2007, now abandoned.

(51) Int. Cl.
*A61B 5/055* (2006.01)
(52) U.S. Cl.
USPC ........... 600/420; 600/407; 600/410; 600/423; 436/173; 436/174; 424/9.3

(58) Field of Classification Search
USPC ................... 62/45.1–54.3; 424/9.3
See application file for complete search history.

(56) References Cited

U.S. PATENT DOCUMENTS 5,809,801 A 9/1998 Cates, Jr. et al.
6,199,385 B1 * 3/2001 Driehuys et al. ............... 62/51.1
(Continued)

FOREIGN PATENT DOCUMENTS

JP 2000507688 A 6/2000
JP 2002526168 A 8/2002
(Continued)

OTHER PUBLICATIONS

Golman et al., Real-time metabolic imaging, Jul. 25, 2006, PNAS vol. 103, No. 30, p. 11270-11275.*

(Continued)

*Primary Examiner* — Paul Hyun
*Assistant Examiner* — Robert Eom
(74) *Attorney, Agent, or Firm* — Joseph J. Christian

(57) ABSTRACT

A fluid path system includes a vial containing a pharmaceutical product therein. A dissolution fluid path is also included in the fluid path system, the dissolution fluid path having an output end in fluid communication with the vial and an input end attached to a pressure vessel containing a dissolution medium. A delivery fluid path is also included in the system having a first end hermetically attached to the vial to transport therefrom a mixture of dissolved pharmaceutical product and dissolution medium and a second end connected to a receiving vessel to receive the mixture. A dissolution fluid path valve is positioned between the pressure vessel and the dissolution fluid path to control flow of the dissolution medium, and a delivery fluid path valve is also included in the fluid path system to control flow of the mixture from the delivery fluid path to the receiving vessel.

25 Claims, 4 Drawing Sheets

(56) References Cited

U.S. PATENT DOCUMENTS

| | | |
|---|---|---|
| 6,237,363 B1 | 5/2001 | Zollinger et al. |
| 6,523,356 B2 | 2/2003 | Hasson et al. |
| 7,102,354 B2 | 9/2006 | Ardenkjaer-Larsen et al. |
| 2004/0066193 A1 | 4/2004 | Ardenkjaer-Larsen et al. |
| 2005/0085682 A1 | 4/2005 | Sasaki et al. |
| 2008/0240998 A1 | 10/2008 | Urbahn et al. |
| 2009/0263325 A1 | 10/2009 | Whitt et al. |

FOREIGN PATENT DOCUMENTS

| | | |
|---|---|---|
| JP | 2002306609 A | 10/2002 |
| JP | 2004512882 A | 4/2004 |
| WO | WO9737177 A1 | 10/1997 |
| WO | WO0237132 A1 | 5/2002 |
| WO | WO2005114244 A1 | 12/2005 |
| WO | 2006011809 A1 | 2/2006 |
| WO | WO2009027645 A2 | 3/2009 |

OTHER PUBLICATIONS

Wilson, "A Vacuum-Tight Sliding Seal", RSI, vol. 12, pp. 91-93, Feb. 1941.

Ardenkjaer-Larsen et al., "Increase in Signal-to-Noise Ratio of Greater Than 10,000 Times in Liquid-State NMR", PNAS, vol. 100, No. 18, pp. 10158-10163, Sep. 2, 2003.

* cited by examiner

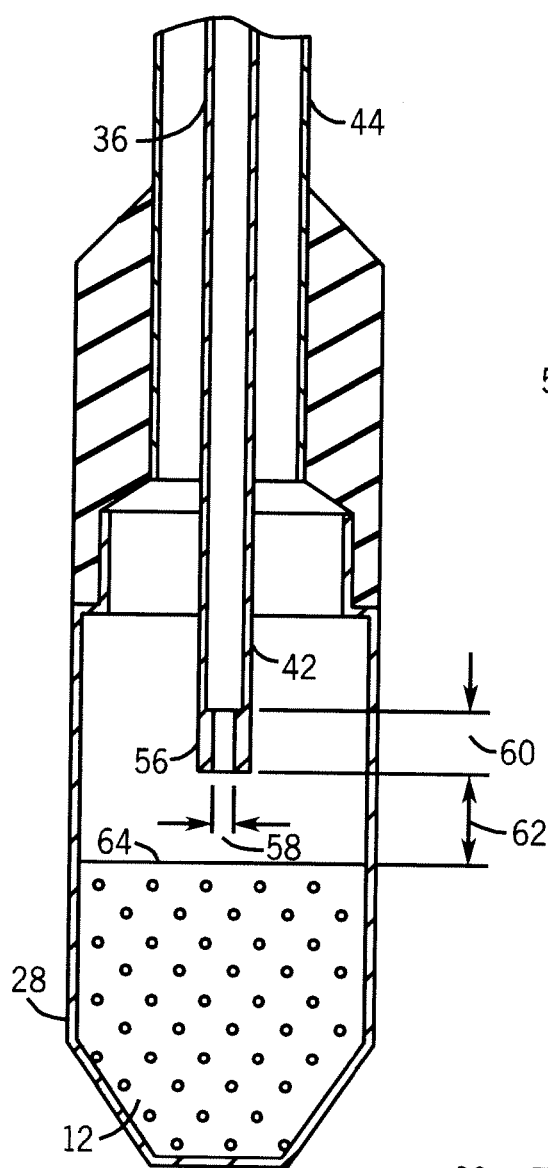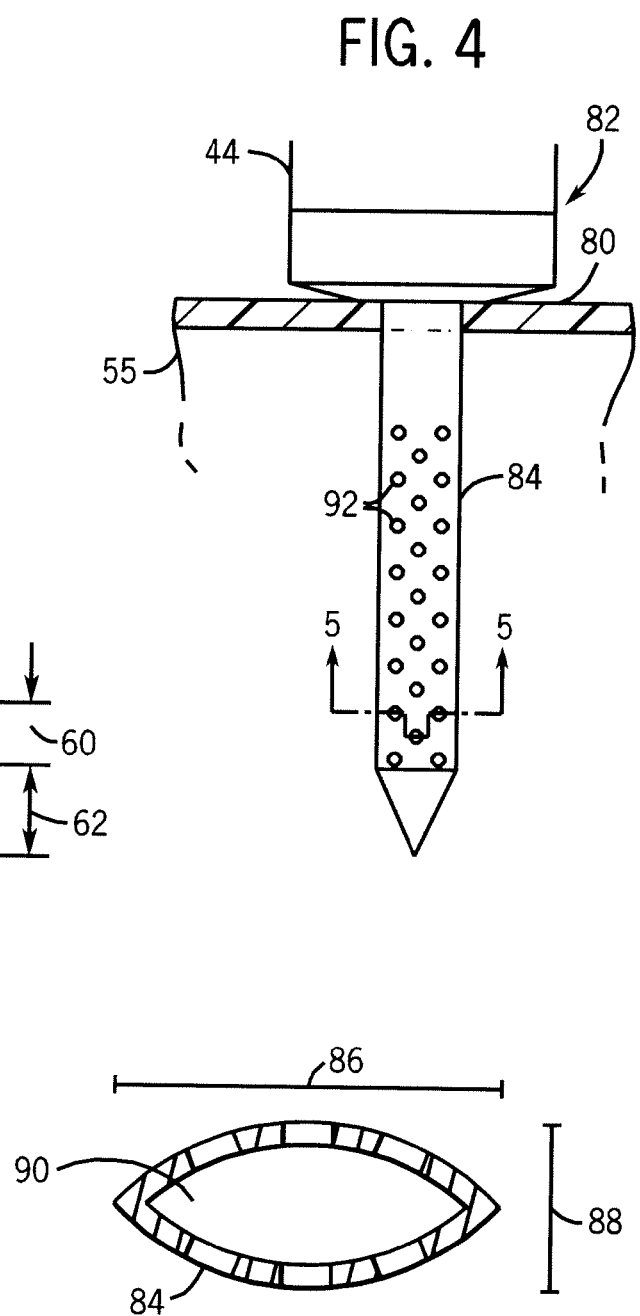

FLUID PATH SYSTEM FOR DISSOLUTION AND TRANSPORT OF A HYPERPOLARIZED MATERIAL

CROSS-REFERENCE TO RELATED APPLICATIONS

This application is a continuation-in-part of U.S. patent application Ser. No. 11/692,642, filed on Mar. 28, 2007, which is herein incorporated by reference.

BACKGROUND OF THE INVENTION

The invention relates generally to a method and apparatus for dissolution and transport of a pharmaceutical product in a fluid path system for use in magnetic resonance imaging (MRI) and analytical high-resolution NMR spectroscopy. MRI is a diagnostic technique that has become particularly attractive to physicians as it is non-invasive and does not involve exposing the patient under study to X-rays associated with other medical imaging techniques. Analytical high resolution NMR spectroscopy is routinely used in the determination of molecular structure.

MRI and NMR spectroscopy can, however, lack sensitivity due to the normally very low polarization of the nuclear spins of the contrast agents typically used. As such, a number of techniques exist to improve the polarization of nuclear spins while in the solid phase. These techniques are known as hyperpolarization techniques and lead to an increase in sensitivity. In hyperpolarization techniques, a sample of an imaging agent, for example $^{13}C_1$-Pyruvate or another similar polarized imaging agent, is introduced or injected into the subject being imaged. As used herein, the term "polarize" refers to the modification of the physical properties of a material for further use in MRI. Further, as used herein, the term "hyperpolarized" refers to polarized at a level over that found at room temperature and at 1 Tesla, which is further described in U.S. Pat. No. 6,466,814.

In many instances, the imaging agent undergoes this hyperpolarization in an apparatus remote from its end use. The hyperpolarized material has a very short life span, and as such, the hyperpolarized material must be quickly transferred from its production source to its place of intended end use (i.e., injection into a patient) and transformed into a useable state. To accomplish this, the cryogenically frozen hyperpolarized material is dissolved into a dissolution medium for injection into the patient. Thus, as a part of a dynamic nuclear polarization (DNP) system, a means for dissolving the polarized sample within the polarizer must be included.

For a sample of polarized acid (e.g., pyruvic acid), it is necessary to use a dissolution medium to dissolve the sample and obtain a solution of polarized sodium salt (e.g., sodium pyruvate) suitable for in vivo injection. The dissolution medium typically is comprised of an aqueous solution including a base (e.g., sodium hydroxide) and a buffering agent (e.g., TRIS hydroxymethyl aminomethane (TRIS)) to dissolve the sample and control/reach a physiologically acceptable pH in the injectate, although the dissolution medium could also be in the form of water.

In the current methodology, a defined volume of dissolution medium containing sodium hydroxide, TRIS-buffer, and EDTA is pressurized with helium gas to a defined pressure in a titanium cylinder and heated to a defined temperature. When the dissolution process is started, the pressurized and heated solvent is released from the cylinder and guided by a continuous helium gas flow into contact with the polarized sample. This method suffers from the drawback that the dissolved sample is mixed with gas as it is ejected into the receiving container and therefore is not sterile for injection. This complicates the removal of the Electron Paramagnetic Agent (EPA) from the dissolved polarized sample and the sterile filtering of the injectate.

Additional problems can arise in existing methodologies that employ fluid path systems to dissolve the frozen sample. That is, one possible failure mode with the current fluid path system involves ensuring that the sample is completely dissolved by the dissolution medium. If the thermal energy, amount, and flow of the dissolution medium is insufficient to completely dissolve the sample, the system may freeze before the sample is dissolved, thus resulting in an ice plug completely blocking flow into and out of the fluid path system. A second failure mode is that the thermal energy transferred to the frozen sample is not sufficient to dissolve the entirety of the sample, resulting in some of the sample being left in a frozen/solid state after a defined volume of dissolution medium has been entered into the fluid path system. This failure to completely dissolve the sample affects the pH level and acid concentration of the injectate in the case of the sample being an acid. For example, pyruvate is a very reactive compound sensitive to both high and low pH (which may catalyze the pyruvate to react), and thus, it is important that the sample be completely dissolved to ensure a desired pH level in the injectate.

Another limitation of current methodology and devices used for dissolving pharmaceutical samples is the cost and complication associated with maintaining a sterile product. For pharmaceutical products, sterility assurance is essential and there can be no risk of contamination to the product. Current methods and devices require the sample to be handled and exposed to the environment. As such, any device in contact with the sample will have to be sterilized and sterility will have to be assured during the dissolution and transport of the sample.

Thus, a need therefore exists for a fluid path system that can rapidly and completely dissolve a frozen hyperpolarized material. It is also desirable that the dissolved material be fully displaced from its initial location to a final location in order to ensure suitable pH levels, acid concentration, and liquid state polarization in the injectable solution. The fluid path system should also provide maintained sterility during dissolution and transport of the material in a cost-effective and efficient manner.

BRIEF DESCRIPTION OF THE INVENTION

The present invention overcomes the aforementioned drawbacks by providing an apparatus and method for dissolution and transport of a pharmaceutical product in a fluid path system. The fluid path system provides for rapid and complete dissolution of a frozen hyperpolarized material and transports the resulting hyperpolarized solution from its initial location within a polarizer system to a final location outside the polarizer system for use (e.g., injection into a patient).

According to one aspect of the present invention a fluid path system is described. The fluid path system comprises a vial to contain a pharmaceutical, a dissolution fluid path having an output end in fluid communication with the vial and an input end attached to a pressure vessel to contain a dissolution medium and a delivery fluid path having a first end hermetically attached to the vial to transport a mixture of dissolved pharmaceutical product and dissolution medium. The dissolution fluid path and delivery fluid path are tubular structures and the dissolution fluid path is positioned internal to or parallel to the delivery fluid path. The fluid path system also comprises a receiving vessel connected to a second end of the delivery fluid path to receive the mixture, a dissolution fluid path valve and a delivery fluid path valve to control flow a filter cartridge integrated within the delivery fluid path to remove at least one of an electron paramagnetic agent (EPA) and a processing agent from the hyperpolarized solution before entering the receiving vessel, and a a sliding seal unit positioned between the pressure vessel and the vial to seal a cryogenically cooled chamber containing the vial from an ambient environment without contacting contents of the vial. The sliding seal is unit bisects the dissolution fluid path and delivery fluid path and is capable of traversing the length of the fluid paths.

In accordance with another aspect of the present invention, a polarizer system to polarize a material to be used in magnetic resonance (MR) imaging includes a cryogenic cooling system to cool a material to be hyperpolarized to a cryogenic temperature and a superconducting magnet positioned about the cryogenic cooling system to create a magnetic field and hyperpolarize the material. The polarizer system also includes a fluid delivery system to dissolve and deliver the hyperpolarized material. The fluid path system being described above.

In accordance with yet another aspect of the present invention, a method of manufacturing a fluid path system includes the steps of hermetically sealing a first end of a delivery fluid path to a vial whereby the delivery fluid path comprises a tubular structure and the vial containing a solid material to be hyperpolarized, positioning a dissolution fluid path within the delivery fluid path, the dissolution fluid path also comprising a tubular structure and having an output end in fluid communication with an interior volume of the vial, connecting a syringe to an input end of the dissolution fluid path, the syringe having a dissolution medium therein, and connecting a receiving vessel to a second end of the delivery fluid path to receive a hyperpolarized solution. The hyperpolarized solution is composed of the dissolution medium and dissolved hyperpolarized material.

Various other features and advantages of the present invention will be made apparent from the following detailed description and the drawings.

BRIEF DESCRIPTION OF THE DRAWINGS

The drawings illustrate an embodiment presently contemplated for carrying out the invention.

In the drawings:

FIG. 2 is cross-sectional view of a vial according to an embodiment of the current invention.

FIG. 4 is a cross-sectional view of a flask and spike according to one embodiment of the current invention.

FIG. 5 is a cross-sectional view taken along 5-5 of FIG. 4.

DETAILED DESCRIPTION OF THE INVENTION

Figure 1:
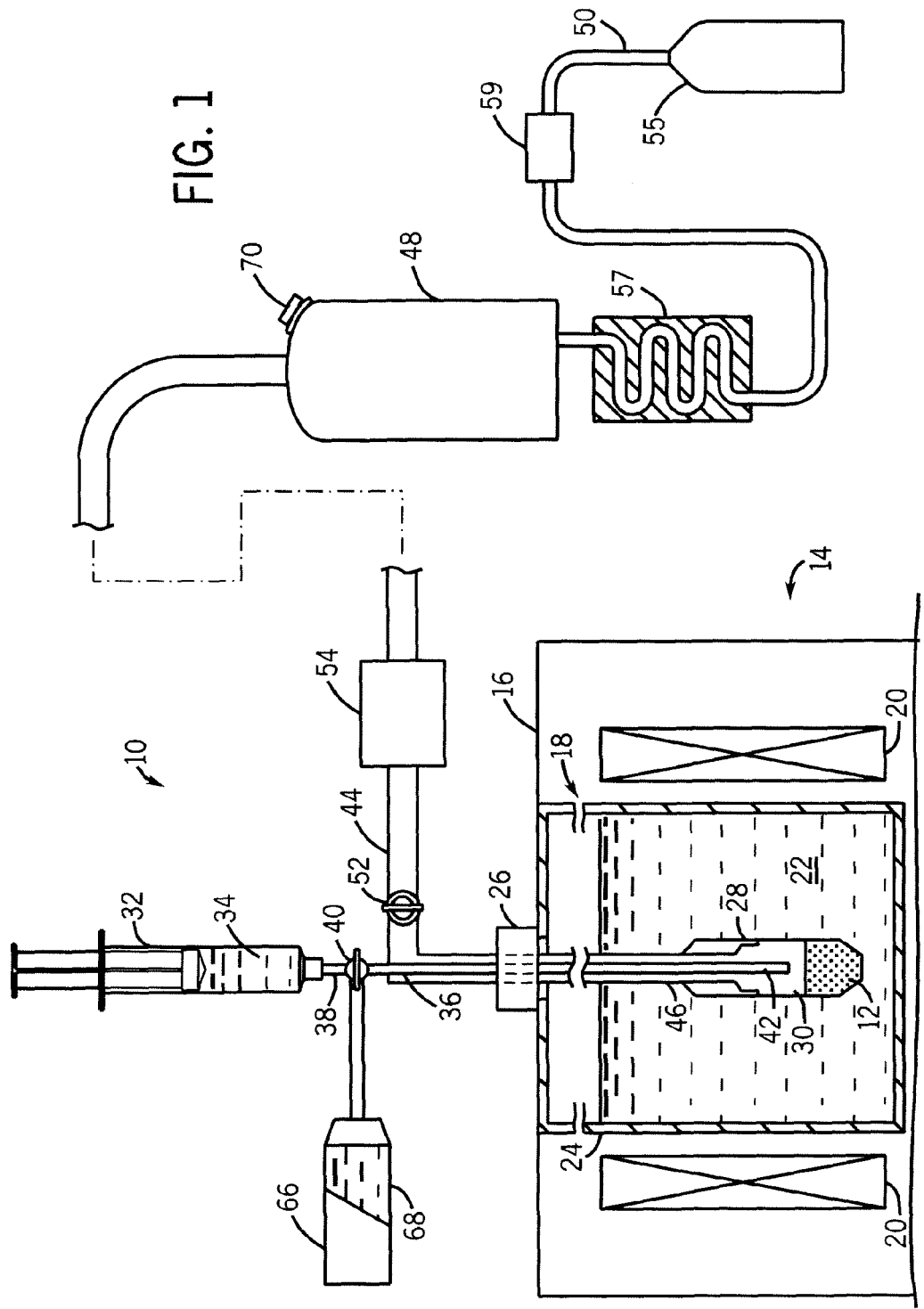
FIG. 1 is a block diagram and schematic of a fluid path system according to an embodiment of the current invention.

Referring to FIG. 1, a fluid path system 10 (i.e., fluid delivery system) is shown for dissolution and transport of a pharmaceutical product. In one embodiment, this pharmaceutical product is a sample 12 of solid hyperpolarized material for use as an imaging agent in magnetic resonance imaging (MRI) and NMR spectroscopy. For example, sample 12 can be composed of $^{13}C_1$-pyruvic acid and EPA, although other imaging agents are also possible. The fluid path system 10 can be made from medical grade materials if used in a clinical setting for preparing and delivering an injectable solution to patients. Such materials are known and are generally plastics of validated quality in terms of leachables and stability. The materials for the fluid path system 10 are further selected on the basis of their thermal, mechanical, and chemical properties to be compatible with the product and environment (cryogenic and superheated temperatures, as well as high pressures). The fluid path system 10 is designed to provide a sterile barrier to the sample and resulting solution and all assemblies and parts therein are designed to prevent the user from unintentionally breaking the barrier. It is further envisioned that the fluid path system 10 can be made as a disposable part (i.e., single use), but can also be re-cycled completely or in part. A single use fluid path system ensures the maximum provision for sterility and patient safety.

Fluid path system 10 is integrated with an apparatus 14 for hyperpolarizing the sample 12. The polarizer apparatus 14 is formed in part by a vacuum chamber 16 that surrounds internal components of the apparatus. Positioned within the vacuum chamber 16 is a system 18 for cryogenically cooling the sample of $^{13}C_1$-pyruvic acid and EPA and a superconducting magnet 20 that together function to hyperpolarize the sample 12. In the embodiment of FIG. 1, the cryogenic cooling system 18 includes a liquid helium bath 22 housed in container 24 to form a cryogenically cooled chamber. The sample 12 is immersed in the liquid helium bath 22 and a magnetic field produced by superconducting magnet 20 to provide conditions for hyperpolarizing the sample 12. Microwave irradiation at an appropriate frequency is provided by a microwave radiation source (not shown) to polarize the solid sample 12 by Dynamic Nuclear Polarization (DNP).

A portion of fluid path system 10 extends down into container 24 of the polarizer apparatus 14. This positioning enables the sample 12 and vial 28 to be exposed to the high magnetic field and cryogenic temperatures of the polarizer apparatus 14. To retain a vacuum within vacuum chamber 16, including container 24, a sliding seal 26 is positioned about that portion of the fluid path system 10 that forms a junction or interface with 24. The sliding seal 26 is configured such that, during operation the fluid path system 10 is allowed to traverse through the seal as needed while still forming an air tight seal. Thus, the vacuum conditions desired in polarizer apparatus 14 for hyperpolarizing sample 12 are maintained by way of sliding seal 26. It is understood, when not configured with the polarizer system, and where the fluid path is held in a fixed position, the sliding seal is capable of movement along the fluid path.

During operation of the polarizer system, the first position of the sliding seal 26 is near the vial, where the sliding seal 26 enables the vial 28 to be interfaced with the polarizer apparatus 14 without compromising vacuum within the vacuum chamber 16, including container 24. In certain embodiments, the length of the outer tube 44 which may traverse the sliding seal 26 is approximately between 10 cm and 100 cm to enable the positioning of the vial 28 in the liquid helium bath 22. During extraction of the fluid path system 10 from the polarizer apparatus 14 the outer tube 44 traverses the sliding seal 26 in the reverse direction returning to the first position where the fluid path system 10 can be removed from the polarizer apparatus 14 without compromising the vacuum.

The sliding seal 26 is positioned between the vial 28 and the fluid path valves 40 and 52 and bisects the inner tube 36 and outer tube 44 without penetrating the physical barrier realized by the wall of the outer tube 44. This positioning of the sliding seal 26 around the outer tube 44 and the barrier the outer tube 44 represents enables a portion of the fluid path system 10 to be positioned within the polarizing apparatus 14 without compromising the sterility of the fluid path system 10 and the sample 12 it contains. Due to the positioning of the sliding seal 26 between the vial 28 and the fluid path valves 40 and 52 makes this component integral to the fluid path system and permanently located on the outer tube 44 between the vial 28 and the fluid path valves 40 and 52. In certain embodiments valves 40 and 52 may be configured as a single valve system that operates to restrict flow independently in tubes 36 and 44.

The sliding seal 26 must embody several potentially opposed characteristics to enable positioning of the sample 12 in the liquid helium bath 22 without degrading the performance of the polarizer apparatus 14. The sliding seal 26 must constrict on outer tube 44 sufficiently to create a vacuum tight barrier. In certain embodiments, leak rates for the sliding seal 26 must be less than or equal to approximately 2.5 mL/hr of air to minimize impact on the internal pressure of the container 24 and the formation of ice within the polarizer apparatus 14. The sliding seal 26 presents a low friction interface with the outer tube 44 to enable the flexible inner tube 36 and outer tube 44 to traverse the sliding seal 26 without bending, buckling or damaging the tubes. The force used to cause the outer tube 44 to traverse the sliding seal 26 should not exceed 25 Newtons.

Furthermore, the sliding seal 26 is capable of operation at cryogenic temperatures. In certain embodiments, during extraction of the fluid path system 10 portions of the outer tube 44 may have been cryogenically cooled by the liquid helium bath 22. As such, the sliding seal 26 must maintain integrity when exposed to low temperatures during cryogenic freezing. In certain application the sliding seal is designed to maintain integrity as low as 10° K. An example of a material and configuration of a seal that meets these characteristics is a Teflon energized lip seal.

The sample 12 positioned within polarizer system 14 is contained in a vial 28 (i.e., sample container), which is formed of a material that is non-reactive to the sample and to other commonly used solvents or solutions that might be used to dissolve the sample 12. The vial 28 can be formed of glass, polymer or another suitable material that would not react with sample 12 or a dissolution medium. Examples of suitable polymers include, but are not limited to polyetherimide, polysulfone and polyetheretherketone. If vial 28 is composed of an electrically conductive material, attention must be paid to the delivery of microwaves for DNP and optionally Nuclear Magnetic Resonance (NMR) detection. A specified quantity or dosage of sample 12 is included in vial 28 to be mixed with a dissolution medium solution and ultimately injected into a patient. Typically, this quantity/dosage of sample 12 will be equal to or less than approximately 2 ml in volume. In certain embodiments to volume of the vial 28 can be increased to contain larger sample doses. The vial 28 is sized so that the quantity of sample 12 included therein fills only a portion of an interior volume 30 of vial 28, with the frozen sample 12 being positioned at the bottom of vial 28. It is also envisioned that the sample 12 could be frozen in other positions in the vial 28, such as coating the walls of the vial to form, for example, a hollow cylinder of sample product.

The vial 28 is included as part of fluid path system 10 that extends down into container 24. In operation, the fluid path system 10 is used to dissolve the cryogenically frozen sample 12 by way of an aqueous solution and transport this dissolved sample out from container 24 to a desired end location, where, in certain applications, it may be injected into a patient. To provide an aqueous solution for dissolving sample 12 in vial 28, a pressure vessel 32 is included in the fluid path system 10. In one embodiment, the pressure vessel is a syringe 32 that can be in the form of a motor powered or pneumatic syringe that produces force to inject a dissolution medium 34 (i.e., buffer solution) into fluid path system 10. Dissolution medium 34 therein is in a heated state to melt and dissolve the cryogenically frozen sample 12 when mixed therewith. Depending on its composition, the dissolution medium 34 can be heated to a temperature of up to approximately 150° C. in a pressure chamber (not shown) or other suitable heating apparatus. The dissolution medium 34 includes a base solvent, such as sodium hydroxide, for neutralizing the pyruvic acid and also possibly an ion chelator (e.g., EDTA). The dissolution medium 34 also includes therein a buffering agent, which commonly is in the form of a buffering salt such as TRIS, although other known buffering salts can also be used. While the dissolution medium 34 listed above is set forth as being composed of sodium hydroxide, EDTA, and TRIS, it is also envisioned that water or other solutions could be used instead.

Attached to syringe 32 is a dissolution fluid path 36 (i.e., inner tube) that forms a fluid path between the syringe 32 and vial 28 containing the sample 12. An input end 38 of inner tube 36 connects to the syringe 32 in a sealed manner. Also positioned near the input end 38 of the inner tube 36, and adjacent to syringe 32, is a dissolution fluid path valve 40 located within inner tube 36. This inner tube valve 40 functions to control a fluid flow of the dissolution medium 34 out from syringe 32 and into the inner tube 36 and allows for a measured amount of dissolution medium 34 to be injected into the fluid path system 10 for dissolving sample 12 and controlling pH of the resulting hyperpolarized solution. An output end 42 of the inner tube 36 extends down into the interior volume 30 of vial 28 and is thus in fluid communication therewith. The inner tube 36 is preferably composed of a material having a low thermal conductivity so as to maintain a temperature in the dissolution medium 34 and minimize the loss of thermal energy therefrom as it passes through inner tube 36 and down into vial 28. In operation, inner tube 36 delivers dissolution medium 34 in a heated state from syringe 32 down into vial 28. In the interior volume 30 of vial 28, the heated dissolution medium 34 comes into contact with frozen sample 12. The dissolution medium 34 dissolves the entirety of the sample 12 to form a mixture that forms a hyperpolarized solution. The resulting hyperpolarized solution is in the form of an intravenous solution that can be directly injected into a patient as approved by qualified health authorities.

A delivery fluid path 44 (i.e., outer tube) is also included in fluid path system 10 to create a separate fluid path from inner tube 36. In one embodiment, and as shown in FIG. 1, inner tube 36 is positioned within outer tube 44, although it is also envisioned that other arrangements could be implemented, such as a side-by-side configuration between the tubes 36, 44 where both are connected to vial 28. The outer tube 44 is also composed of a low conductivity material, the material preferably having a different thermal conductivity than inner tube 36, to prevent heat transfer between not only inner tube 36 and outer tube 44, but also between outer tube 44 and the surrounding environment of container 24 and the low temperatures present therein due to liquid helium bath 22. A first end 46 of outer tube 44 is hermetically sealed to vial 28 to form a fluid connection therebetween that is free of leaks. As stated above, a hyperpolarized solution is formed from the dissolution medium 34 and the dissolved sample 12 and is contained in the interior volume 30 of vial 28. As more dissolution medium 34 is injected into inner tube 36 and down into vial 28 to dissolve sample 12, the quantity of hyperpolarized solution increases and is forced out of vial 28. The hyperpolarized solution thus flows up into outer tube 44 forming an outer fluid path for transport of the hyperpolarized solution. The hyperpolarized solution flows through outer tube 44 and eventually into a receiving vessel 55 (i.e., flask) attached to a second end 50 of outer tube 44, where it collects until the desired amount of hyperpolarized solution has been created. Outer tube 44 can be integrally connected to, or separately fitted on; flask 55 and can also include a nozzle (not shown) on second end 50 that enters into flask 55. In certain embodiments tube 46 may be configured as a separate tube from tube 44 and oriented in series with tube 44.

To control flow of the hyperpolarized solution between vial 28 and flask 55, a delivery fluid path valve 52 is placed within outer tube 44. In one embodiment, this outer tube valve 52 is positioned close to syringe 32. In certain embodiments the delivery fluid path valve 52 prevents the flow of air or liquid from container 48 into tube 44 and vial 28. This flow may be induced by temperature induced pressure differentials within fluid path system 10 due to the cryogenic cooling of vial 28.

The outer tube valve 52 is disposable and can be replaced in the fluid path system 10 as needed. Also included within outer tube 44 is a filter cartridge 54 that removes an electron paramagnetic agent (EPA) from the hyperpolarized solution and possibly other processing agents that may have been added to hyperpolarize the sample 12. The EPA filter cartridge 54 removes the EPA from the hyperpolarized solution to make it suitable for injection. Furthermore, EPA filter cartridge can function as a heat sink to cool the hyperpolarized solution down to a lower temperature more suitable for injection into the patient.

After passing through EPA filter cartridge 54, the hyperpolarized solution passes through outer tube 44 and optionally into holding container 48, where it can be held for a short time to mix the solution and where automated quality control tests can be performed as desired. In one embodiment, further cooling of the hyperpolarized solution can be performed in holding container 48 by reducing pressure therein and/or by diluting the solution with a quantity of water for injection (e.g., 10 ml) that is at room temperature. The water can already be present in container 48 or added thereto upon the accumulation of the hyperpolarized solution. The pressure reduction and the addition of the water would provide any further cooling necessary to bring the temperature of the resulting hyperpolarized solution from about 80° C. to 50° C., although it is also envisioned that the temperature of the solution can be brought down even further via these methods to a temperature point suitable for injection (e.g. ~38° C.).

After mixing and cooling of the hyperpolarized solution, the solution is forced out from holding container 48 and travels down outer tube 44 to a receiving vessel 55 (i.e., flask) before final injection into a patient. It is envisioned that a heat exchanger can be connected to outer tube 44 between holding container 48 and flask 55 to further cool the hyperpolarized solution (if necessary) down to a temperature threshold set at 38° C. for injection of the solution into the patient. As stated above, the temperature of the hyperpolarized solution may be in the range of 50° C. when it exits holding container 48.

As the hyperpolarized solution remains in its hyperpolarized state for only a short time period (e.g. approximately 1 minute), in certain embodiments, as shown in FIG. 1, an optional heat exchanger 57 may be used. The heat exchanger allows for further cooling of the solution in a quick and efficient manner. The heat exchanger 57 is constructed in part of a material having superior heat conduction properties, such as copper, to allow for the solution to pass through the heat exchanger 57 in a minimum amount of time (i.e., having a high flow capacity) while still removing a large amount of heat therefrom. While copper provides the desired heat transfer properties, it is neither sterility nor liquid state polarization compliant. As such, the copper surfaces in heat exchanger 57 that are in contact with the hyperpolarized solution are gold plated to form a more sterile and non-reactive fluid path. To further fulfill sterility requirements associated with the injectable hyperpolarized solution, the heat exchanger 57 is also designed to be easily disassembled for cleaning, with all components and compartments in the heat exchanger being accessible. In certain embodiments the heat exchanged may be composed of porous polymeric fits with high surface area. In one embodiment, the polymer may be polyethylene. In certain embodiments the polymeric frit based heat exchange may be disposable. As such, heat exchanger 57 can be formed into two detachable halves to accommodate easy assembly and disassembly, or some other similar configuration.

It is also envisioned that heat exchanger 57 be a single use disposable part along with the rest of fluid path system 10. In certain embodiments, the heat exchanger 54 may be position between the filter cartridges 54 the holding container 48. The heat exchanger 57 also is free of dead ends or other areas where the hyperpolarized solution could become trapped so as to minimize loss of the solution as it passes therethrough. As stated above, the heat exchanger 57 may be optional and its inclusion in fluid path system 10 will depend on the temperature of the dissolution medium in syringe 32 and the thermal mass of other components in the system.

Upon exiting heat exchanger 57, it is envisioned that the hyperpolarized solution can pass down outer tube 44 and through an additional sterile filter 59. Filter 59 can be optionally added to fluid path system 10 to further ensure sterilization of the hyperpolarized solution, although it is recognized that fluid path system 10 is designed as a sterile system without the inclusion of filter 59. The filter 59 can be composed of a membrane and/or resin and can take the form of filters known in the art and as used for sterile filtering of intravenous solutions and injectable drugs. After exiting filter 59, the solution then passes into flask 55. Additional dissolution medium or water for injection can be added to flask 55 (or already be present in the flask) to mix with the hyperpolarized solution as desired to create a desired temperature, concentration, and/or pH level. The temperature, concentration, and pH of the hyperpolarized solution in flask 55 can then be measured by an operator to ensure it is at or below the threshold temperature of 38° C. and at a suitable pH and concentration for injection into the patient.

As set forth above, the inclusion of heat exchanger 57 and filter 59 in fluid path system 10 is optional. It is also envisioned that holding container 48 be optional as well and that fluid path system 10 may be configured to provide hyperpolarized solution having a desired temperature directly to receiving vessel/flask 55, or that the functions of holding container 48 could be implemented into flask 55. In certain embodiments additional dissolution medium or water for injection can be added to container 48 to mix with the hyperpolarized solution as desired to create a desired temperature, concentration, and/or pH level. The temperature, concentration, and pH of the hyperpolarized solution in container 48 may then be measured by an operator to ensure it is at or below the threshold temperature of 38° C. and at a suitable pH and concentration, such as for example the correct temperature and pH for injection into the patient.

To assist in dissolution of sample 12 in fluid path system 10, a nozzle 56 is positioned at output end 42 of inner tube 36 and positioned, at least in part, within vial 28. As shown in FIG. 2, nozzle 56 is positioned within vial 28 and adjacent to the hyperpolarized sample 12 so that when dissolution medium 34 exits the nozzle 56, it comes directly into contact with sample 12. The nozzle 56 aids in producing fluid flow characteristics in the dissolution medium 34 that are needed to completely and efficiently dissolve sample 12 and then force that resulting hyperpolarized solution out from vial 28 and into outer tube 44, and eventually to holding container 48 and flask 55.

Several factors in regard to the nozzle 56 configuration and placement affect the dissolution of hyperpolarized sample 12. That is, nozzle 56 can be designed to have a nozzle diameter 58 and depth 60 that will create desired fluid flow characteristics for dissolution of the sample 12, and can be placed a selected distance 62 from sample 12. In one embodiment, it is envisioned that the nozzle diameter 58 is 0.9 mm and is attached to an inner tube 36 having an outer diameter of 1.83 mm. The inner tube 36 is positioned within outer tube 44, which is formed to hermetically seal to vial 28, the outer tube 44 having an inner diameter of 2.69 mm. The nozzle 56 also has a depth 60 of 1-3 mm. The diameter measurements set forth above result in a ratio of flow areas of approximately 1.6. Such a ratio, along with the nozzle depth selected above, results in a desirable fluid flow of the dissolution medium 34 for dissolving sample 12 and for forcing the mixture of dissolution medium and dissolved sample (i.e., the hyperpolarized solution) out from the vial 28.

Placement of nozzle 56 as compared to sample 12 also affects dissolution efficiency. The distance 62 between a surface 64 of the sample 12 and the nozzle 56 (i.e., "standoff") not only affects dissolution efficiency, but is also important in ensuring that segments of the sample 12 do not break off and clog the nozzle 56 and the inner tube 36, thus interrupting fluid flow in the fluid path system 10. That is, if the nozzle 56 is placed too closely to the surface 64 of sample 12, the sample 12 may melt and refreeze to block the nozzle 56 before dissolution medium 34 is injected therethrough. In one embodiment, standoff 62 is set to 5 mm and is combined with the nozzle dimensions set forth above. This combination of the standoff measurement and nozzle dimensions provides one specific configuration in which dissolution of the hyperpolarized sample 12 is achieved in a desired manner. While specific measurements have been provided for nozzle diameter 58 and depth 60, and for standoff 62 between the nozzle 56 and sample surface 64, it is envisioned that other suitable measurement values and flow area ratios can also be implemented. The exact values (i.e., measurements and distances) decided upon for these features when designing fluid path system 10 will be based on at least one of the values of: temperature of the dissolution medium 34, pressure of the dissolution medium 34, and quantity of the hyperpolarized sample 12. The standoff distance 62 can also be determined in part by the nozzle diameter 58. The exact fluid flow characteristics/ratios and standoff desired will be dependent, at least in part, on these factors.

The nozzle 56 itself can be attached to first end 42 of inner tube 36 in several ways. One method of placing nozzle 56 at output end 42 of inner tube 36 includes placing a separate and distinct nozzle component on inner tube 36. Nozzle 56 would be placed on inner tube 36 before insertion of the inner tube 36 within outer tube 44 and vial 28. Nozzle 56 can also be formed on output end 42 of inner tube 36 from the inner tube material, which is composed of a formable polymer material. That is, nozzle 56 can be formed by heating the inner tube polymer material to a temperature where it will flow. A needle (not shown) having an outer diameter equal to the desired nozzle diameter 58 is inserted inside inner tube 36 and the melting inner tube polymer material flows in towards the needle. When allowed to cool, a nozzle or orifice having a certain length and diameter will be formed. The exact diameter 58 and depth 60 of the nozzle 56 can thus be determined by the configuration of the needle inserted into inner tube 36 and the nozzle 56 can be formed to provide fluid flow characteristics desired in the fluid path system 10.

Referring back to FIG. 1, in certain embodiments an optional vessel 66 containing an additional processing agent 68 may be included in fluid path system 10 to aid in polarization of sample 12. In one embodiment, vessel 66 contains a gadolinium solution 68. Prior to polarization of the sample 12, gadolinium solution 68 is injected into inner tube 36 and down into vial 28 to aid and improve hyperpolarization of the sample 12. That is, before sample 12 is brought down to a cryogenic temperature by liquid helium bath 22, gadolinium solution 68 is released from vessel 66, through a syringe valve 40, which is configured as a 3-way valve, and forced into inner tube 36 by helium gas used to pressurize vessel 66. The gadolinium solution 68 is forced down through inner tube 36 by this helium gas pressure and enters into vial 28 to mix with sample 12. The helium gas atmosphere present in vial 28 blankets the mixing of the gadolinium solution 68 and sample 12 to allow for proper mixing to occur. Any excess gas volume would be forced through a ventilation port present in the fluid path system 10, such as a ventilation port 70 in holding container 48. Upon proper mixing of the gadolinium solution 68 and sample 12, the prepared sample is brought down to a cryogenic temperature by liquid helium bath 22 and introduced into a magnetic field for hyperpolarization as described above. Inclusion of vessel 66 in fluid path system 10 is optional and is only needed if a compound or ingredient is to be added to sample 12 before the polarization thereof.

Figure 3:
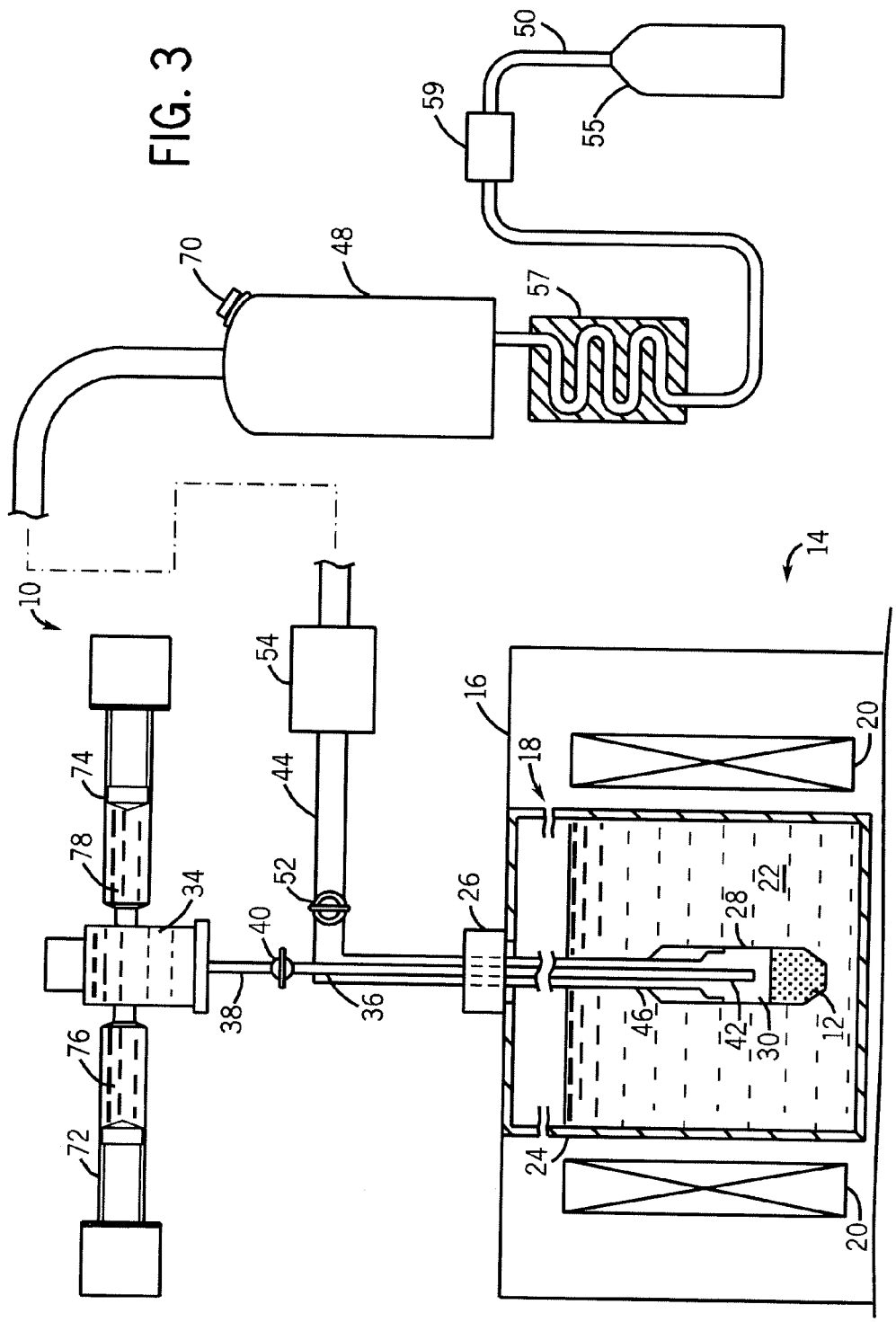
FIG. 3 is a schematic of a portion of a fluid path system according to another embodiment of the current invention.

Referring now to FIG. 3, another embodiment of fluid path system 10 is shown as including dual syringes or injectors 72, 74 for providing dissolution medium 34 to the system 10 for dissolving the hyperpolarized sample 12. This two syringe arrangement can be implemented if better control of pH than otherwise possible is required due to, for example, requirements to control pH, filtration, or the stability of sample 12. The dissolution medium 34 is divided into two parts, one part containing an aqueous solution of the base 76 needed to neutralize the pyruvic acid of sample 12. The second part of dissolution medium 34 is comprised of an aqueous solution of buffer salt 78 (e.g., TRIS). The two dissolution medium components 76, 78 are placed in two motor powered or pneumatic syringes 72, 74, which are both connected to inner tube 36 of the fluid path system 10. At least one of the bases 76 and the buffering salt 78 are heated to an appropriate temperature to allow for melting and dissolution of the hyperpolarized sample 12. When the dissolution process is started, both syringes 72, 74 dispense their contents into inner tube 36. The dispensing of the base 76 and aqueous buffer salt 78 by the dual syringes 72, 74 is electronically controlled so as to control the concentration of the base 76 in the dissolution medium 34. That is, the amount of base 76 injected into the inner tube 36 to mix with the buffer salt 78 is controlled in such a manner that the base 76 is continuously matched by a stoichiometric amount of dissolved pyruvic acid of sample 12. When the hyperpolarized sample 12 is completely dissolved, only the syringe 74 containing the aqueous solution of buffer salt will continue to dispense fluid into the inner tube 36. The aqueous buffer salt 78 would then drive the bolus (i.e., hyperpolarized solution) through outer tube 44 and filter 54, and into holding container 48.

As shown in FIG. 4, in one embodiment of flask 55, the flask includes a rubber septum 80 fitted over an inlet port thereof. A spike 82 composed of a non-metallic material is fitted to second end 50 of outer tube 44 and is configured to penetrate the septum 80 to transfer hyperpolarized solution from the outer tube 44 to flask 55. The hyperpolarized solution is forced from the outer tube 44 through the spike 82 and into the flask 55. The spike 82 allows the flask 55 to be easily and rapidly removed from fluid path system 10 once a desired quantity of hyperpolarized solution has been transferred into the flask 55.

As shown in FIG. 5, the spike 82 includes an elliptical needle 84 having a greater diameter 86 of 3.0 mm along one axis and a lesser diameter 88 of 0.3 mm along another axis. Referring back to FIG. 4, the elliptically designed needle 84 penetrates the septum 80, having a thickness of about 32 mm for example, with more of a cut-like incision as opposed to a circular needle, and as such, reduces force on the septum 80 and the needle 84 during insertion therein. While having an elliptical design with a decreased diameter along one axis, the rigidity of the needle 84 is such as to give it the strength to withstand the forces imparted thereon during insertion through the septum 80. Furthermore, the needle 84 is sized so as not to negatively impact the flow rate of the hyperpolarized solution between the outer tube 44 and the flask 55. In an alternative embodiment the spike 82 and needle 84 may be positioned on outer tube 44 and inside of container 48.

Also included in the needle 84 of the spike 82 is a fluid path 90 (shown in FIG. 5) and fluid path holes 92 vertically spaced along the length of the needle 84 so as to form a fluid connection between outer tube 44 and flask 55. The fluid path holes 92 are designed to act as spray nozzles/jets that diffuse the hyperpolarized solution as the solution is forced through the holes 92. The diffusion caused by the fluid path holes 92 provides for improved homogenization of the hyperpolarized solution, as a larger portion of the solution is forced in different directions. The diffusion also results in a greater surface area of the solution being exposed, which enables a reduction in the hyperpolarized solution temperature before injection into a patient.

Figure 6:
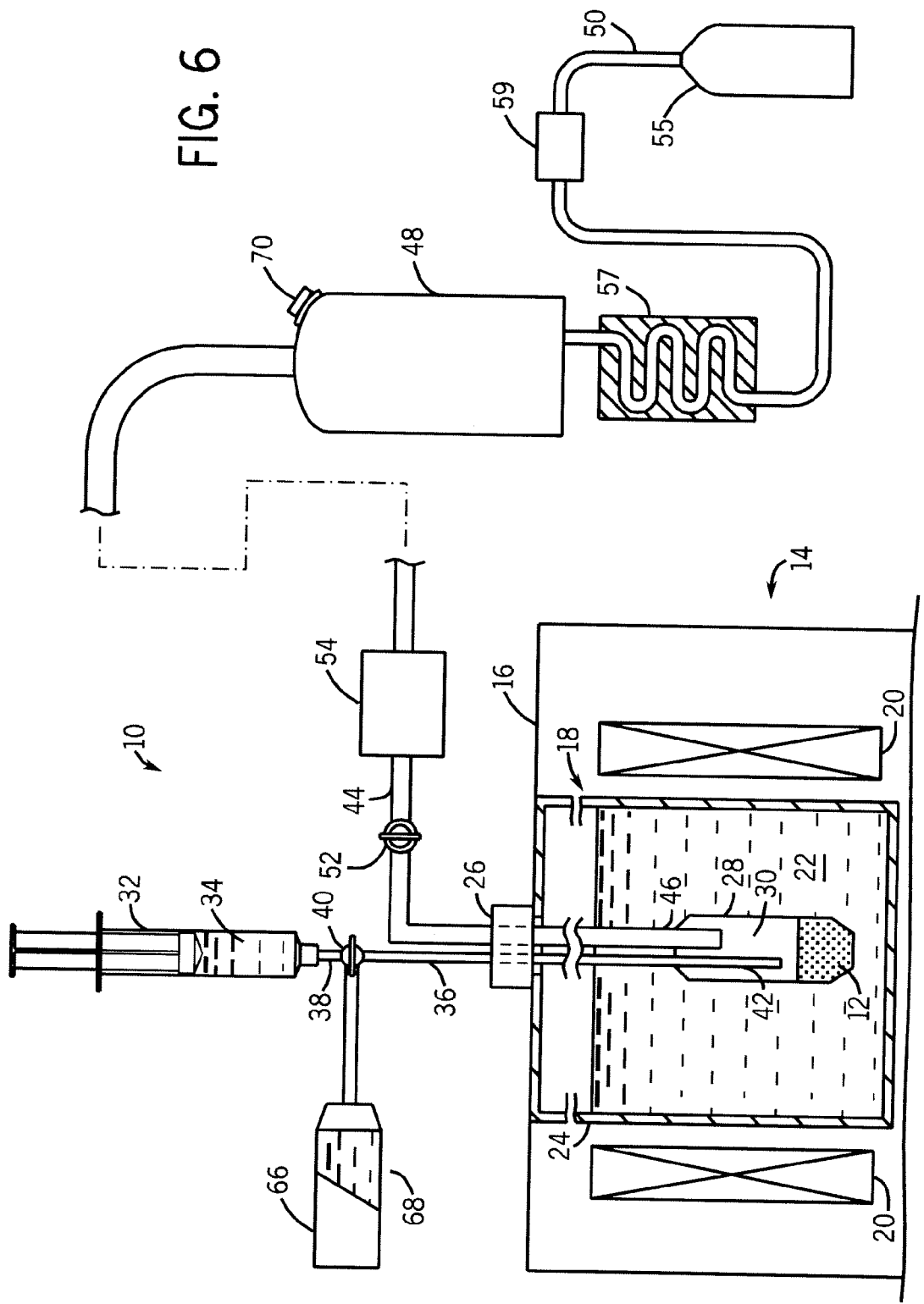
FIG. 6 is a block diagram and schematic of a fluid path system according to an embodiment of the current invention.

While the fluid path system 10 described above includes an inner tube 36 and outer tube 44, as shown in FIG. 1, it is also envisioned that other configurations can also be implemented. Referring now to FIG. 6, fluid path system 10 is configured to have a dissolution fluid path 36 and delivery fluid path 44 positioned in a parallel arrangement. In such an arrangement it is understood that the sliding seal is capable of traversing the length of both the delivery fluid path and the dissolution fluid path, as both bisect the sliding seal unit. Dissolution fluid path is in fluid communication with vial 28 to transfer dissolution medium from syringe 32 into the vial to dissolve sample 12. Delivery fluid path is sealed to vial 28 to transfer a mixture of the dissolution medium 34 and dissolved sample 12 out from the vial in the form of a hyperpolarized solution to be delivered to flask 55 as desired.

Therefore, according to one embodiment of the present invention, a fluid path system includes a vial containing a pharmaceutical product therein, a dissolution fluid path having an output end in fluid communication with the vial and an input end attached to a pressure vessel containing a dissolution medium, and a delivery fluid path having a first end hermetically attached to the vial to transport therefrom a mixture of dissolved pharmaceutical product and dissolution medium. The fluid path system also includes a holding container connected to a second end of the delivery fluid path to receive the mixture, a dissolution fluid path valve positioned between the pressure vessel and the dissolution fluid path to control flow of the dissolution medium, and a delivery fluid path valve to control flow of the mixture from the delivery fluid path to the holding container.

In accordance with another embodiment of the present invention, a polarizer system to polarize a material to be used in magnetic resonance (MR) imaging includes a cryogenic cooling system to cool a material to be hyperpolarized to a cryogenic temperature and a superconducting magnet positioned about the cryogenic cooling system to create a magnetic field and hyperpolarize the material. The polarizer system also includes a fluid delivery system to dissolve and deliver the hyperpolarized material. The fluid delivery system further includes a sample container containing the material to be hyperpolarized therein, a syringe containing a dissolution medium therein, and an inner tube connected to the syringe to receive and transport the dissolution medium therethrough, wherein the inner tube is in fluid communication with the sample container that has an inner volume in which the dissolution medium and the hyperpolarized material are in fluid contact. The fluid delivery system also includes an outer tube hermetically connected to the sample container to convey a hyperpolarized solution out from the sample container that is comprised of the dissolution medium and dissolved hyperpolarized material.

In accordance with yet another embodiment of the present invention, a method of manufacturing a fluid path system includes the steps of hermetically sealing a first end of an outer tube to a vial containing a solid material to be hyperpolarized therein and positioning an inner tube within the outer tube, the inner tube having an output end in fluid communication with an interior volume of the vial. The method also includes the steps of connecting a syringe having a dissolution medium therein to an input end of the inner tube and connecting a holding container to a second end of the outer tube to receive a hyperpolarized solution therein, wherein the hyperpolarized solution is composed of the dissolution medium and dissolved hyperpolarized material.

The present invention has been described in terms of the preferred embodiment, and it is recognized that equivalents, alternatives, and modifications, aside from those expressly stated, are possible and within the scope of the appending claims.

What is claimed is:

1. A fluid path system comprising:
   a vial to contain a pharmaceutical product therein;
   the pharmaceutical product positioned within the vial wherein said pharmaceutical product comprises a material to enhance contrast in at least one of magnetic resonance (MR) imaging and nuclear magnetic resonance (NMR) spectroscopy;
   a dissolution fluid path having an output end in fluid communication with the vial and an input end attached to a pressure vessel to contain a dissolution medium used to dissolve said pharmaceutical product forming a mixture;
   a dissolution medium positioned within the pressure vessel wherein said dissolution medium comprises a base solution and a buffering agent;
   a delivery fluid path having a first end hermetically attached to the vial to transport therefrom a mixture of the dissolved pharmaceutical product and the dissolution medium;
   wherein the dissolution fluid path and the delivery fluid path are tubular structures and the dissolution fluid path is positioned internal to or parallel to the delivery fluid path;

a receiving vessel connected to a second end of the delivery fluid path to receive the mixture;

a dissolution fluid path valve positioned between the pressure vessel and the dissolution fluid path to control flow of the dissolution medium;

a delivery fluid path valve to control flow of the mixture from the delivery fluid path to the receiving vessel;

a filter cartridge integrated within the delivery fluid path to remove at least one of an electron paramagnetic agent (EPA) and a processing agent from the mixture before entering the receiving vessel; and a sliding seal unit positioned between the pressure vessel and the vial to seal a cryogenically cooled chamber containing the vial therein from an ambient environment without contacting contents of the vial, and wherein said sliding seal unit bisects the dissolution fluid path and the delivery fluid path and is capable of traversing the length of said fluid paths.

2. The fluid path system of claim 1 further comprising a nozzle attached to the output end of the dissolution fluid path to modify a fluid flow of the dissolution medium into the vial.

3. The fluid path system of claim 2 wherein the nozzle is comprised of a formable polymer material.

4. The fluid path system of claim 2 wherein the nozzle includes a nozzle diameter and a nozzle depth based on at least one of a composition of the dissolution medium to be added to the dissolution fluid path, a temperature of the dissolution medium to be added to the dissolution fluid path, a pressure of the dissolution medium to be added to the dissolution fluid path, and a quantity of the pharmaceutical product to be added to the vial.

5. The fluid path system of claim 1 wherein the pressure vessel is a syringe.

6. The fluid path system of claim 1 wherein the dissolution fluid path and the delivery fluid path are comprised of a material having a low thermal conductivity.

7. The fluid path system of claim 6 wherein the dissolution fluid path is formed of a material having a different thermal conductivity than the material from which the delivery fluid path is formed.

8. The fluid path system of claim 1 wherein the sliding seal unit comprises a material capable of forming a vacuum seal with a leak rate of less than or equal to 2.5 ml/hr.

9. The fluid path system of claim 8 wherein the material is teflon.

10. The fluid path system of claim 1 wherein the sliding seal unit exerts a force on the delivery fluid path less than or equal to 25 Newtons.

11. The fluid path system of claim 1 wherein the dissolution fluid path valve and the delivery fluid path valve are comprised of a single valve system that operates to restrict flow independently in the dissolution fluid path and the delivery fluid path.

12. The fluid path system of claim 1 wherein the pharmaceutical product comprises pyruvic acid.

13. The fluid path system of claim 1 wherein each of the vial, the dissolution fluid path, the delivery fluid path, and the receiving vessel are composed of sterile medical grade materials to form a sterile environment for the mixture.

14. A polarizer system to polarize a material to be used in magnetic resonance (MR) imaging, the system comprising:

a cryogenic cooling system to cool a material to be hyperpolarized to a cryogenic temperature;

a superconducting magnet positioned about the cryogenic cooling system to create a magnetic field and hyperpolarize the material; and a fluid delivery system to dissolve and deliver the material, the fluid delivery system comprising:

a vial to contain a pharmaceutical product therein;

a pharmaceutical product positioned within the vial wherein said pharmaceutical product comprises a material to enhance contrast in at least one of magnetic resonance (MR) imaging and nuclear magnetic resonance (NMR) spectroscopy;

a dissolution fluid path having an output end in fluid communication with the vial and an input end attached to a pressure vessel to contain a dissolution medium used to dissolve said pharmaceutical product forming a mixture;

a dissolution medium positioned within the pressure vessel wherein said dissolution medium comprises a base solution and a buffering agent;

a delivery fluid path having a first end hermetically attached to the vial to transport therefrom a mixture of the dissolved pharmaceutical product and the dissolution medium;

wherein the dissolution fluid path and delivery fluid path are tubular structures and the dissolution fluid path is positioned internal to or parallel to the delivery fluid path;

a receiving vessel connected to a second end of the delivery fluid path to receive the mixture;

a dissolution fluid path valve positioned between the pressure vessel and the dissolution fluid path to control flow of the dissolution medium;

a delivery fluid path valve to control flow of the mixture from the delivery fluid path to the receiving vessel;

a filter cartridge integrated within the delivery fluid path to remove at least one of an electron paramagnetic agent (EPA) and a processing agent from the mixture before entering the receiving vessel; and a sliding seal unit positioned between the pressure vessel and the vial to seal a cryogenically cooled chamber containing the vial therein from an ambient environment without contacting contents of the vial, and wherein said sliding seal unit the dissolution fluid path and the delivery fluid path and is capable of traversing the length of said fluid paths.

15. The polarizer system of claim 14 further comprising a nozzle attached to the output end of the dissolution fluid path to modify a fluid flow of the dissolution medium into the vial.

16. The polarizer system of claim 14 wherein the nozzle is comprised of a formable polymer material.

17. The polarizer system of claim 16 wherein the nozzle includes a nozzle diameter and a nozzle depth based on at least one of a composition of the dissolution medium to be added to the dissolution fluid path, a temperature of the dissolution medium to be added to the dissolution fluid path, a pressure of the dissolution medium to be added to the dissolution fluid path, and a quantity of the pharmaceutical product to be added to the vial.

18. The polarizer system of claim 14 wherein the pressure vessel is a syringe.

19. The polarizer system of claim 14 wherein the dissolution fluid path and the delivery fluid path are comprised of a material having a low thermal conductivity.

20. The polarizer system of claim 19 wherein the dissolution fluid path is formed of a material having a different thermal conductivity than the material from which the delivery fluid path is formed.

21. The polarizer system of claim 14 wherein the sliding seal unit comprises a material capable of forming a vacuum seal with a leak rate of less than or equal to 2.5 ml/hr.

22. The polarizer system of claim 21 wherein the material is teflon.

23. The polarizer system of claim 14 wherein the sliding seal unit exerts a force on the delivery fluid path less than or equal to 25 Newtons.

24. The polarizer system of claim 14 wherein the dissolution fluid path valve and the delivery fluid path valve are comprised of a single valve system that operates to restrict flow independently in the dissolution fluid path and the delivery fluid path.

25. The polarizer system of claim 14 wherein the pharmaceutical product comprises pyruvic acid.

* * * * *

UNITED STATES PATENT AND TRADEMARK OFFICE
CERTIFICATE OF CORRECTION

PATENT NO.         : 8,731,640 B2                                     Page 1 of 1
APPLICATION NO.    : 13/350189
DATED              : May 20, 2014
INVENTOR(S)        : Urbahn et al.

It is certified that error appears in the above-identified patent and that said Letters Patent is hereby corrected as shown below:

In the Specification

Column 3, Line 12, delete "biscects" and insert -- bisects --, therefor.

Column 8, Line 14, delete "polymeric fits" and insert -- polymeric frits --, therefor.

Column 8, Line 24, delete "exchanger 54" and insert -- exchanger 57 --, therefor.

In the Claims

Column 14, Line 40, in Claim 14, delete "unit the" and insert -- unit bisects the --, therefor.

Signed and Sealed this
Second Day of December, 2014

Michelle K. Lee
*Deputy Director of the United States Patent and Trademark Office*